United States Patent [19]

Hermecz et al.

[11] 4,321,377
[45] Mar. 23, 1982

[54] SUBSTITUTED-4-OXO-1,6,7,8-TETRAHYDRO-4H-PYRIDO[1,2-a]PYRIMIDINES

[75] Inventors: István Hermecz; Zoltán Mészáros; István Bitter; Ágnes Horváth; Lelle Vasvári née Debreczy, all of Budapest, Hungary

[73] Assignee: Chinoin Gyógyszer és Vegyészeti Termékek Gyára Rt., Budapest, Hungary

[21] Appl. No.: 35,279

[22] Filed: May 2, 1979

[51] Int. Cl.$^3$ .............. C07D 471/04; A61K 31/505
[52] U.S. Cl. .................... 544/282; 424/251; 544/238
[58] Field of Search .......................... 544/282

[56] References Cited

U.S. PATENT DOCUMENTS

| 3,853,871 | 12/1974 | Agata et al. | 544/282 |
| 3,898,224 | 8/1975 | Yale et al. | 544/282 |
| 3,960,847 | 6/1976 | Yale | 544/282 |
| 3,960,863 | 6/1976 | Sato et al. | 424/282 |
| 4,022,897 | 5/1977 | Yale et al. | 544/282 |
| 4,066,766 | 1/1978 | Kadin | 544/238 |
| 4,209,622 | 1/1980 | Mészáros et al. | 544/282 |
| 4,252,807 | 2/1981 | Hermecz et al. | 544/282 |

Primary Examiner—Donald G. Daus
Assistant Examiner—James H. Turnipseed
Attorney, Agent, or Firm—Karl F. Ross

[57] ABSTRACT

Nitrogen bridgehead compounds (pyrido-[1,2-a]-pyrimidine derivatives) which are useful intermediates in the making of known compounds of this class and which themselves possess PG-antagonist, analgesic, antiartheriosclerotic, tranquilizing and like pharmaceutical activity.

4 Claims, No Drawings

SUBSTITUTED-4-OXO-1,6,7,8-TETRAHYDRO-4H-PYRIDO[1,2-a]PYRIMIDINES

FIELD OF THE INVENTION

The present invention relates to new nitrogen bridgehead compounds and process for the preparation thereof.

It has been disclosed that 2-methyl-4-oxo-6,7,8,9-tetrahydro-4H-pyrido[1,2-a]pyrimidine-9-carboxylic derivatives may be prepared by catalytic hydrogenation of the suitable unsaturated compounds (J. Het. Chem. 13, 797; 1976).

DESCRIPTION OF THE INVENTION

The compounds of the invention are new and have the Formula wherein
R is hydrogen or $C_{1-4}$ alkyl,
$R^1$ is hydrogen or $C_{1-4}$ alkyl or
R and $R^1$ together form a —(CH=CH)$_2$ group attached to the two adjacent ring carbon atoms and the dotted line stands for a chemical bond,
$R^2$ is hydrogen, $C_{1-4}$ alkyl,
$R^3$ is hydrogen, $C_{1-4}$ alkyl, phenyl, carboxy or alkali metal salt thereof, alkoxycarbonyl containing $C_{1-6}$ alkoxy, carbamoyl, cyano, —CO—N-H—CO—SO$_2$—C$_6$H$_4$—p—CH$_3$ or —(CH$_2$)$_s$—COOR$^{14}$— wherein s=1, 2 or 3 and $R^{14}$ is hydrogen or $C_{1-4}$ alkyl,
n is 0 or 1;
(a) if $R^{13}$ is hydrogen and $R^{12}$ and $R^{11}$ and $R^9$ and $R^{10}$ together form a chemical bond then
Y is a stripped oxygen or sulfur atom and $R^7$ and $R^8$ stand for a lone electron-pair or
Y is a stripped nitrogen atom,
$R^7$ is $C_{1-4}$ alkyl, substituted or unsubstituted $C_{6-10}$ aryl or $C_{7-12}$ aralkyl,
$R^8$ is a lone electron-pair or $C_{1-4}$ alkyl and in this latter case a halide ion forms a salt with the positive nitrogen atom,
X ($R^4$, $R^5$, $R^6$) is halogen or
X is a stripped oxygen or sulfur atom,
$R^4$ is hydrogen or $C_{1-4}$ alkyl,
$R^5$ and $R^6$ represent an unshared electron-pair or
X is a stripped nitrogen atom and
$R^4$ is chloroacetyl, $C_{1-4}$ alkyl, substituted or unsubstituted $C_{6-10}$ aryl or substituted or unsubstituted heteroaryl,
$R^5$ is hydrogen or alkyl and
$R^6$ is a lone electron-pair or
(b) if $R^{12}$ and $R^{13}$ together form a chemical bond and $R^{11}$ is hydrogen and $R^9$ and $R^{10}$ together form a chemical bond, then
$R^4$, $R^5$, $R^6$, $R^7$, $R^8$, X and Y are as defined in item (a) and
(c) if $R^{10}$ and $R^{11}$ and $R^{12}$ and $R^{13}$ together form a chemical bond, then
Y is a stripped oxygen or sulfur and if $R^7$, $R^8$ and $R^9$ stand for an unshared electron-pair, then a positive cation forms a salt with the thus formed anion or
$R^8$ and $R^9$ stand for an unshared electron-pair,
$R^7$ is hydrogen or $C_{1-4}$ alkyl or
Y is a stripped nitrogen atom,
$R^7$ is hydrogen, $C_{1-4}$ alkyl, substituted or unsubstituted $C_{6-10}$ aryl,
$R^8$ is a $C_{1-4}$ alkyl,
$R^9$ stands for a lone electron-pair,
X ($R^5$, $R^6$, $R^7$) is halogen or
X represents a stripped oxygen or sulfur atom and if $R^4$, $R^5$ and $R^6$ stand for a lone electron-pair, then a positive cation forms a salt with the thus formed anion or
$R^4$ is hydrogen or $C_{1-4}$ alkyl,
$R^5$ and $R^6$ stand for an unshared electron-pair or
X is a stripped nitrogen atom and $R^4$ is chloroacetyl, $C_{1-4}$ alkyl, substituted or unsubstituted $C_{6-10}$ aryl or substituted heteroaryl,
$R^5$ is hydrogen or $C_{1-4}$ alkyl and
$R^6$ is an unshared electron-pair and
if Y and X are stripped oxygen or sulfur and $R^5$, $R^6$, $R^7$, $R^8$ and $R^9$ represent a lone electron-pair or
Y and X are stripped nitrogen and $R^6$ and $R^9$ is a lone electron-pair, $R^5$ and $R^8$ are hydrogen or $C_{1-4}$ alkyl, then
$R^4$ and $R^7$ form an optionally substituted —(CH$_2$)$_s$— wherein s stands for 1, 2, 3 or 4.

Preferred are those compounds of the formula I, wherein n=1, R is hydrogen, $R^1$ is hydrogen or $C_{1-4}$ alkyl, particularly methyl, $R^2$ is hydrogen and $R^3$ is carboxy, methoxy carbonyl, ethoxy-carbonyl or carbamoyl.

A preferred group of compounds of the formula (I) is the specific group of compounds of the formula (I')

or a tautomer, optically active antipode, or pharmaceutically acceptable salt thereof wherein
R, $R^1$ and $R^2$ are each hydrogen or $C_1$ to $C_4$ alkyl;
$R^3$ is carboxy, $C_1$ to $C_6$ alkoxycarbonyl, carbamoyl, cyano, —CONH——SO$_2$—C$_6$H$_4$—p—CH$_3$ or —(CH$_2$)$_s$—COOR$^{14}$ wherein s is 1, 2 or 3 and $R^{14}$ is hydrogen or $C_1$ to $C_4$ alkyl;
X is halogen, —OR$^4{}_1$, —SR$^4{}_1$ wherein $R^4{}_1$ is hydrogen or $C_1$ to $C_4$ alkyl, or
X is —N($R^4$)($R^5$) wherein
$R^4$ is chloroacetyl, $C_1$ to $C_4$ alkyl, tosyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen;
$R^5$ is hydrogen or $C_1$ to $C_4$ alkyl; and Y is oxygen, sulfur, or =N—$R^7$ wherein $R^7$ is $C_1$ to $C_4$ alkyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen.

Another preferred group of the compounds of formula (I) is the specific group of compounds of the formula (I″)

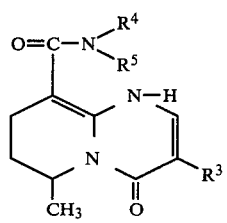

or a tautomer, optically active antipode or pharmaceutically acceptable salt thereof wherein $R^3$ is hydrogen, $C_1$ to $C_4$ alkyl, phenyl, carboxy, $C_1$ to $C_6$ alkoxycarbonyl, carbamoyl, cyano, CONH—$SO_2$—$C_6H_4$—p—$CH_3$ or $(CH_2)_s$—$COOR^{14}$ wherein s is 1, 2 or 3 and $R^{14}$ is hydrogen or $C_1$ to $C_4$ alkyl;

$R^4$ is chloroacetyl, $C_1$ to $C_4$ alkyl, tosyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen; and $R^5$ is hydrogen or $C_1$ to $C_4$ alkyl.

The invention further provides a process for the preparation of the compounds of the formula

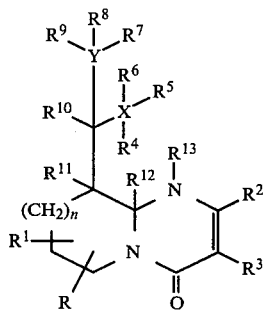

wherein the substituents are as defined above, optically active antipodes and salts thereof. The method comprises reacting a nitrogen bridgehead compound of the formula

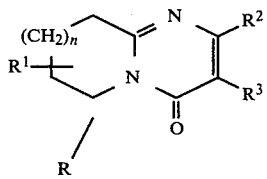

defined above.

(a₁) with a dihalogeno methylene ammonium halide of the formula

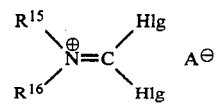

wherein
Hlg is halogen,
$R^{15}$ is $C_{1-4}$ alkyl or substituted or unsubstituted $C_{6-10}$ aryl,
$R^{16}$ is $C_{1-4}$ alkyl or
A stands for an anion, obtaining thus a nitrogen bridgehead compound of the formula

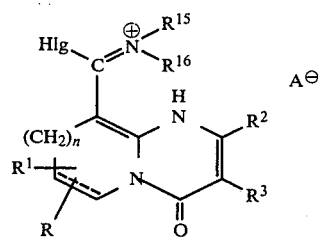

(a₂) with a carbon disulfide of the formula $$CS_2 \qquad IV$$

preferably in the presence of alkali ions und obtaining thus compounds of the formula

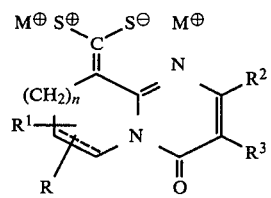

wherein M is an alkali-metal ion- or
(a₃) with an isocyanate of the formula $$R^{17}—N=C=V \qquad V$$

wherein $R^{17}$ is $C_{1-4}$ alkyl, chloroacetyl, substituted or unsubstituted $C_{6-10}$ aryl or substituted or unsubstituted heteroaryl, V stands for oxygen or sulfur and obtaining thus a compound of the formula

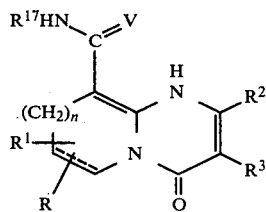

and converting any of the compounds of the formulae Ia, Ib, Ic obtained by any of the process variants, if desired, to a different compound of the formulae Ia, Ib, Ic or I and converting a substituent $R^2$, $R^3$, $R^4$, $R^5$, $R^6$, $R^7$, $R^8$, $R^9$, $R^{10}$, $R^{11}$, $R^{12}$, $R^{13}$, X or Y in the obtained compound of the formula I, if desired, into another $R^2$, $R^3$, $R^4$, $R^5$, $R^6$, $R^7$, $R^8$, $R^9$, $R^{10}$, $R^{11}$, $R^{12}$, $R^{13}$, X or Y in an optional order and/or converting it to a pharmaceutically acceptable salt or setting it free from its salt and/or resolving, if desired, the racemate of the formula I.

We have unexpectedly found that compounds of the general formula II contain active hydrogens in the methylene group which is in the beta position related to the nitrogens and these active hydrogens are suitable for electrophilic substitution reactions. Thus compounds of the formula I exhibit valuable biological activity and serve as starting materials for the preparation of valuable biologically active compounds. Thus nitrogen bridgehead compounds of the formula I and derivatives thereof can be used in therapy.

The prepared compounds of the formula I may exist in three tautomeric forms:

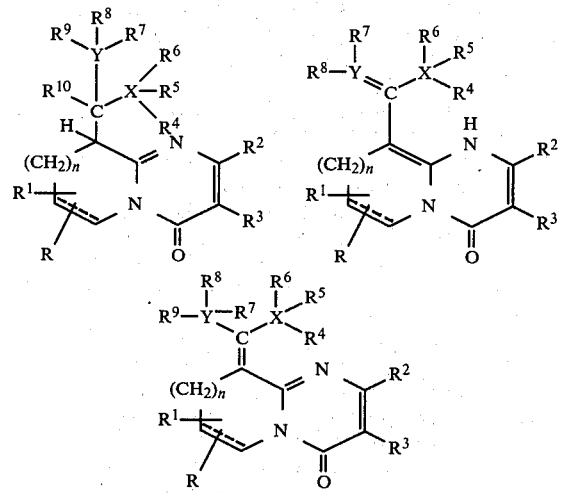

FIG. 1

Depending upon the nature of the substituents one or another tautomeric form may predominate or two tautomeric forms under given circumstances may form an equilibrium mixture which may be shown by spectroscopic methods. Each tautomeric form may exist in the form of Z-E geometric isomers too. In the Examples the prepared products are named considering the prevailing form.

The present invention includes the possible geometric isomers and racemic and optically active forms of the nitrogen bridgehead compounds of the formula I.

In process step ($a_1$) the nitrogen bridgehead compound of the general formula II is added to a solution of dihalogeno methylene ammonium halide in an inert solvent; the compound of the formula II may be dissolved, if desired, in an inert solvent, and the reaction is completed by heating. The formed nitrogen bridgehead compound of the formula Ia is preferably isolated by evaporating the reaction mixture followed by crystallization of the residue.

The reaction of the process step ($a_1$) is carried out in an inert solvent, such as hydrocarbons, preferably benzene, toluene, xylene, or chlorinated hydrocarbons, such as chloroform, dichloromethane, chlorobenzene, etc. The reaction is carried out at a temperature of 0°–180° C., preferably at 10°–120° C. The formed compound of the formula Ia may be converted to a compound of the formula I by reacting it for example with an amine, without isolation.

The process step ($a_2$) is preferably carried out by adding dropwise an alcoholic solution of alkali hydroxide under mild external cooling to an alcoholic solution of the nitrogen bridgehead compound of the formula II and carbondisulfide of the formula IV and stirring the reaction mixture preferably at room temperature. The compounds of the formula Ib formed in the reaction are recovered, if desired, by removing the solvent at reduced pressure. According to another preferable embodiment of the process variant the formed compound of the formula Ib is converted to a compound of the formula I without isolation by using, for example alkylating agents.

As alcohols preferably methanol, ethanol, n- or isopropanol or n-butanol may be employed. As the alkali hydroxide, sodium or potassium hydroxide is preferred. The reaction is preferably carried out at 0° to 120° C. To 1 mole of nitrogen bridgehead compound of the formula II 1 to 5 moles of carbon disulfide of the formula IV are used.

According to process step ($a_3$) the nitrogen bridgehead compound of the formula II may be reacted with an isocyanate of the formula V without any solvent or in the presence of an inert solvent. If a solvent is used the formed compound of the formula Ic is precipitating from the reaction mixture and may be removed by filtration. If the formed compound of the formula Ic does not precipitate from the reaction mixture then the mixture is evaporated at a reduced pressure and the obtained residue is recrystallized from a suitable solvent. If the reaction is carried out without solvent, the reaction mixture is crystallized from a suitable solvent when the reaction is completed. The reaction is carried out at 0°–250° C. The reaction temperature depends on the starting materials. For 1 mole of nitrogen bridgehead compound of the formula II, 1 to 3 moles of the isocyanate of the formula V are used.

A given compound of the general formula I wherein R, $R^1$, $R^2$, $R^3$, n and the dotted line are as given above, $R^{10}$ and $R^{11}$ and $R^{12}$ and $R^{13}$ together form a chemical bond, X and Y are sulfur and $R^4$, $R^5$, $R^6$, $R^7$, $R^8$, $R^9$ represent an unshared electron-pair and an alkali metal cation forms a salt with the forming anion—is reacted (a) with an alkylating agent to obtain a compound of the formula I—wherein R, $R^1$, $R^2$, $R^3$, n and the dotted line are as defined above, $R^9$ and $R^{10}$ and $R^{11}$ and $R^{12}$ together form a chemical bond, $R^{13}$ stands for hydrogen, X and Y stand for sulfur, $R^5$, $R^6$, $R^7$ and $R^8$ represent an unshared electron-pair, $R^4$ stands for $C_{1-4}$ alkyl. As alkylating agents, alkyl halides, such as methyl iodide, ethyl bromide, etc., aralkyl halides, such as benzyl chloride, dialkylsulfates, such as dimethylsulfate, diethylsulfate, trialkylphosphates, such as triethylphosphate, benzene sulfonic acid and p-toluene-sulfonic acid alkyl esters, trialkyl oxonium fluoroborates, may be used.

The reaction is preferably carried out in the presence of a solvent at 0° to 160° C. As solvents the solvents usually used in alkylation or aralkylation reactions are suitable.

For 1 mole of starting material of the formula I preferably 0.3–2.0 mole of alkylating or aralkylating agent is used depending on the nature of the used alkylating or aralkylating agent. The molar ratio of the reactants may be changed, if desired; or (b) with an alkylene halide and thus compounds of the formula I are obtained—wherein R, $R^1$, $R^2$, $R^3$, n and the dotted line are as defined above, $R^{10}$ and $R^{11}$ and $R^{12}$ and $R^{13}$ together form a chemical bond, X and Y stand for sulfur and $R^5$, $R^6$, $R^8$, $R^9$ stand for a lone electron-pair and $R^4$ and $R^7$ together form $-(CH_2)_s$ wherein s is 1, 2, 3 or 4. The reaction may preferably be carried out under the circumstances mentioned under item (a).

A given compound of the formula I—wherein R, $R^1$, $R^2$, $R^3$, n and the dotted line are as given above, and $R^9$ and $R^{10}$ and $R^{11}$ and $R^{12}$ together form a chemical bond, $R^{13}$ represents hydrogen, X and Y represent sulfur, $R^5$, $R^6$, $R^7$, $R^8$ stand for a lone electron-pair, $R^4$ is a $C_{1-4}$ alkyl, $C_{7-12}$ aralkyl, is (a) reacted with an alkylating agent, preferably in the presence of an acid binding agent and thus such compounds of the formula I are obtained—wherein R, $R^1$, $R^2$, $R^3$, n and the dotted line are as given above, $R^{10}$ and $R^{11}$ and $R^{12}$ and $R^{13}$ together form a chemical bond, X and Y stand for sulfur and $R^5$, $R^6$, $R^8$ and $R^9$ represent an unshared electron-pair, $R^4$ and $R^7$ stand for identical or different $C_{1-4}$ alkyl.

As alkylating agents the same agents may be used as mentioned above. As acid binding agents alkali carbonate, alkali hydrogen carbonate, alkali hydroxide, trialkylamine, alkali earth metal carbonate are preferred.

The reaction is preferably carried out in the presence of a solvent.

The reaction is carried out under the conditions given above.

(b) The latter compound of formula I can be heated with acid anhydride and forming thus a 1,3-dithiethane ring from two

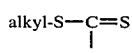

groups or an aralkyl-S-C=S group and obtaining thus a compound of the formula

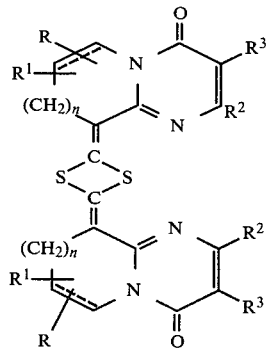

Id wherein R, $R^1$, $R^2$, $R^3$, n and the dotted line are as defined above. As acid anhydrides preferably aliphatic acid anhydrides, such as acetic acid anhydride, propionic acid anhydride may employed. The reaction is preferably carried out at the boiling point of the acid anhydride.

(c) The same compound of formula I is reacted with diamine to obtain thus such a compound of the formula I—wherein R, $R^1$, $R^2$, $R^3$, n and the dotted line are as defined above, $R^{10}$ and $R^{11}$ and $R^{12}$ and $R^{13}$ together form a chemical bond, X and Y stand for a stripped nitrogen atom, $R^6$ and $R^9$ represent an unshared electron-pair, $R^5$ and $R^8$ stand for hydrogen or $C_{1-4}$ alkyl, $R^4$ and $R^7$ together form an optionally substituted $-(CH_2)_s$ group, wherein s is 1, 2, 3 or 4.

A given compound of the formula I—wherein R, $R^1$, $R^2$, $R^3$, n and the dotted line are as defined above, $R^9$ and $R^{10}$ and $R^{11}$ and $R^{12}$ together form a chemical bond, $R^{13}$ is hydrogen, X ($R^4$, $R^5$, $R^6$) is halogen, Y is a stripped nitrogen, $R^7$ is a $C_{1-4}$ alkyl, substituted or unsubstituted $C_{6-10}$ aryl, $R^8$ is $C_{1-4}$ alkyl and a halide ion forms a salt with the positive nitrogen—is (a) reacted with alcohol in the presence of an alkali alkanoate to yield compounds of the formula I are obtained, wherein R, $R^1$, $R^2$, $R^3$, n and the dotted line are as defined above, $R^{13}$ stands for hydrogen, $R^9$ and $R^{10}$ and $R^{11}$ and $R^{12}$ form a chemical bond, X and Y stand for a stripped oxygen, $R^5$, $R^6$, $R^7$, $R^8$ stand for a lone electron-pair, $R^4$ is $C_{1-4}$ alkyl.

As alcohols, aliphatic or aralkyl alcohols may be used. As alkali alkanoate, salts of alkali metals with aliphatic carboxylic acids are preferred. Sodium acetate and calcium acetate may also be employed.

The reaction is preferably carried out at a temperature between 0° to 150° C.

(b) The same compound of Formula I can be reacted with water containing alcohol and thus compounds of the formula I are obtained wherein R, $R^1$, $R^2$, $R^3$, n and the dotted line are as defined above, $R^{13}$ is hydrogen, $R^9$ and $R^{10}$ and $R^{11}$ and $R^{12}$ form a chemical bond, X is a stripped nitrogen, Y is stripped nitrogen atom and $R^6$, $R^7$ and $R^8$ represent an unshared electron-pair, $R^4$ is $C_{1-4}$ alkyl, substituted or unsubstituted $C_{6-10}$ aryl, $R^5$ is $C_{1-4}$ alkyl.

As the alcohol, preferably an aliphatic alcohol is used.

The reaction may be carried out at 0° to 150° C., preferably at the boiling point of the alcohol used.

(c) The same compound of Formula I is reacted with a primary or secondary amine preferably in the presence of an inert solvent and thus such compounds of the formula I are obtained—wherein R, $R^1$, $R^2$, $R^3$, n and the dotted line are as given above, $R^9$ and $R^{10}$, $R^{11}$ and $R^{12}$ form a chemical bond, $R^{13}$ is hydrogen, X and Y represent a stripped nitrogen atom, $R^4$ is $C_{1-4}$ alkyl, substituted or unsubstituted $C_{6-10}$ aryl, substituted or unsubstituted heteroaryl, $R^5$ is hydrogen, $C_{1-4}$ alkyl, $R^6$ represents an unshared electron-pair, $R^7$ stands for $C_{1-4}$ alkyl, substituted or unsubstituted $C_{6-10}$ aryl, $R^8$ is $C_{1-4}$ alkyl and a halide ion forms a salt with the positive nitrogen and the base is set free from the obtained salt if desired, and thus such compounds of the formula I are obtained, wherein R, $R^1$, $R^2$, $R^3$, n and the dotted line are as defined above, $R^{10}$ and $R^{11}$ and $R^{12}$ and $R^{13}$ together form a chemical bond, X and Y represent a stripped nitrogen atom, $R^4$ is hydrogen, $C_{1-4}$ alkyl, substituted or unsubstituted $C_{6-10}$ aryl or substituted or unsubstituted heteroaryl, $R^5$ is hydrogen or $C_{1-4}$ alkyl or $R^7$ is $C_{1-4}$ alkyl, substituted or unsubstituted $C_{6-10}$ aryl, $R^8$ is $C_{1-4}$ alkyl and $R^6$ and $R^9$ represent an unshared electron-pair. The reaction may be carried out at 0° to 160° C., preferably at the boiling point of the used inert solvent.

As inert solvents aromatic hydrocarbons, such as benzene, toluene, etc. halogenated hydrocarbons, such as dichloromethane, chloroform, carbon-tetrachloride, chlorobenzene can be used. 1 to 5 moles, preferably 1.9–2.9 moles of ammonia or amine may be used related to 1 mole of the starting nitrogen bridgehead compound.

The obtained nitrogen bridgehead compound of the formula I may be set free by using carbonates, alkali hydrogen carbonate, alkali hydroxide or trialkylamine.

(d) The same compound of formula I can be reacted with a diamine preferably in the presence of an inert solvent to obtain such nitrogen bridgehead compounds of the formula I wherein R, $R^1$, $R^2$, $R^3$, n and the dotted line are as defined above and $R^{10}$ and $R^{11}$ and $R^{12}$ and $R^{13}$ form a chemical bond, X and Y represent a stripped nitrogen atom, $R^6$ and $R^9$ represent an unshared electron-pair, $R^5$ and $R^8$ stand for hydrogen or $C_{1-4}$ alkyl, and $R^4$ and $R^7$ together form an substituted or unsubstituted group of the formula $-(CH_2)_s$ wherein s is 2, 3 or 4.

The reaction may be carried out under the conditions given under item (c).

The term "$C_{1-4}$ alkyl" used in the specification includes straight or branched alkyl. The term "$C_{6-10}$ aryl" stands for phenyl or naphthyl, which can be substituted with one or more of the same or different substituents selected from $C_{1-4}$ alkyl, $C_{1-4}$ alkoxy, amino, hydroxy, carboxylic acid, carboxylic acid derivative, nitro and halogen. The term "$C_{1-4}$ alkoxy" includes straight and branched alkyl-containing alkoxy. The term "carboxylic acid derivative" includes alkoxycarbonyl containing $C_{1-4}$ alkoxy, nitrile, amino-carbonyl optionally substituted on the amino group by $C_{1-4}$ alkyl, $C_{1-4}$ acyl, ($C_{1-4}$ dialkyl amino methylene)heteroaryl amino and carbohydrazido. The term "heteroaryl" includes monocyclic or bicyclic compounds containing one or more of the same or different heteroatoms, which can be substituted by alkyl, nitro, alkoxy, amino or halogen (such as 2-, 3- or 4-pyridyl, furyl, pyrimidinyl, pyrazinyl, pyridazinyl, etc.).

Heterocyclic compounds of the formula II used as starting material may be prepared by methods disclosed in Hungarian Pat. Specifications Nos.: 156.119, 158.085, 162.384, 162.373 and 166.577 and Dutch Patent Application No. 7 212 286 and the compounds of the formulae III, IV and V or the compounds used for the preparation thereof are commercially available products.

The salts of the compounds of the formula I may be alkali salts formed on the carboxy group, such as sodium or potassium salts, ammonium salts, alkali earth metal salts, such as calcium or magnesium salts and salts formed with amines, such as triethylamine.

The compounds of the formula I are primarily useful as pharmaceutical intermediate products. The compounds may be converted to pyrido-[1,2-a]pyrimidine derivatives substituted in the 9-position by a hydrazono group by reacting them with aryl diazonium salts and the obtained end products exhibit pharmaceutical activity, for example antiallergic activity. Compounds of the formula I themselves show PG-antagonistic, analgesic, antiatheriosclerotic tranquilizer or other activity.

If the compounds of the formula I are used in therapy, then the effective amount of drug supplied daily may vary from 1–1500 mg. administered once or in divided dose(s) depending upon the field of use.

The compounds of the formula I may be formulated in the form of dragées, tablets, capsules, injections, suspensions, injections, powders, suppositories or other forms and may contain the usual additives, such as disintegrating agents and carriers.

Further details of our invention are illustrated by the following Examples which are given for illustration and not for limitation.

EXAMPLE 1

5.9 g. of 3-ethoxy-carbonyl-6-methyl-4-oxo-6,7,8,9-tetrahydro-4H-pyrido[1,2-a]pyrimidine and 2.3 ml. of carbon disulfide are dissolved in 35 ml. of ethanol and to the solution of 2.8 g. potassium hydroxide in 25 ml. of ethanol is added dropwise at 25°–30° C. The reaction mixture is stirred for 1 hour at room temperature and evaporated at reduced pressure and thus 9.7 g. of 3-ethoxycarbonyl-6-methyl-9-[(bis-thiolate)-methylene]-4-oxo-6,7,8,9-tetrahydro-4H-pyrimidine dipotassium salt are obtained.

EXAMPLE 2

To a solution of 9.7 g. of dipotassium salt of 3-ethoxycarbonyl-6-methyl-9-[(bis-thiolate)-methylene]-4-oxo-6,7,8,9-tetrahydro-4H-pyrido[1,2-a]pyrimidine (prepared in Example) 1 in 60 ml. of ethanol 4.7 ml. dimethylsulfate is added dropwise under external cooling and the reaction mixture is stirred for 1 hour at 40° C. The precipitated clear yellow crystals are filtered, washed with water and dried. 7.1 g. (86%) of 3-ethoxycarbonyl-6-methyl-9-(methylthio-thiocarbonyl)-4-oxo-1,6,7,8-tetrahydro-4H-pyrido[1,2-a]pyrimidine are obtained, the product melts at 198°–199° C. after recrystallization from benzene.

Analysis: for the formula $C_{14}H_{18}N_2O_3S_2$; calculated: C: 51.51%; H: 5.56%; N: 8.58%; found: C: 51.70%; H: 5.78%; N: 8.48%.

EXAMPLE 3

To 60 ml. of an ethanol solution of 9.7 g. of dipotassium salt of 3-ethoxycarbonyl-6-methyl-9-[(bis-thiolate)-methylene]-4-oxo-6,7,8,9-tetrahydro-4H-pyrido[1,2-a]-pyrimidine prepared according to Example 1 4.7 g. of ethylene bromide are added. The reaction mixture is stirred for 1 hour at 40° C. and the precipitated sodium bromide is filtered. The mother liquor is evaporated to half volume and the crystals precipitated upon colling are filtered and washed with water and dried. 3 g. of 3-ethoxycarbonyl-6-methyl-9-[1,3-dithiolane-2-ylidene]-4-oxo-6,7,8,9-tetrahydro-4H-pyrido[1,2-a]pyrimidine are obtained, the product melts at 205°–207° C. after recrystallization from ethanol.

Analysis: for the formula $C_{15}H_{18}N_2O_3S_2$; calculated: C: 53.23%; H: 5.36%; N: 8.27%; found: C: 53.17%; H: 5.41%; N: 8.22%.

EXAMPLE 4

3.26 g. of 3-ethoxycarbonyl-6-methyl-9-(methylthio-thiocarbonyl)-4-oxo-1,6,7,8-tetrahydro-4H-pyrido[1,2-a]pyrimidine are heated in 20 ml. of acetic acid anhydride for 2 hours. The crystals precipitated after cooling are filtered and washed with benzene and dried. 1.6 g. (57.6%) of 3-ethoxy-carbonyl-6-methyl-9-[4-(3-ethoxycarbonyl-6-methyl-4-oxo-6,7,8,9-tetrahydro-4H-pyrido[1,2-a]pyrimidine-9-ylidine]-1,3-dithiethane-2-ylidene)-4-oxo-6,7,8,9-tetrahydro-4H-pyrido[1,2-a]pyrimidine is obtained which melts at 315°–318° C. after recrystallization from dimethylformamide.

Analysis: for the formula $C_{26}H_{28}N_4O_6S_2$; calculated: C: 56.10%; H: 5.07%; N: 10.07%; S: 11.52%; found: C: 55.89%; H: 4.98%; N: 10.20%; S: 10.80%.

EXAMPLE 5

To a mixture of 16.3 g. of phosgene-N,N-dimethyliminium-chloride in 50 ml. dichloromethane 23.6 g. of 3-ethoxycarbonyl-6-methyl-4-oxo-6,7,8,9-tetrahydro-4H-pyrido[1,2-a]pyrimidine in 30 ml. of dichloromethane is added dropwise under stirring and the reaction mixture is heated for 3 hours. When the solvent is distilled off the residual substance is crystallized with ether.

35.2 g. of highly hygroscopic 3-ethoxycarbonyl-6-methyl-9-[(chloro-N,N-dimethylammonio)-methylene]-4-oxo-6,7,8,9-tetrahydro-4H-pyrido[1,2-a]pyrimidine chloride is obtained and dried in vacuo.

Analysis: for the formula $C_{15}H_{20}N_3O_3Cl_2$; calculated: $Cl_{ionic}$: 19.6%; found: $Cl_{ionic}$: 19.4%.

EXAMPLE 6

A solution of 1.8 g. of 3-ethoxycarbonyl-6-methyl-9-[(chloro-N,N-dimethylammonio)-methylene]-4-oxo-6,7,8,9-tetrahydro-4H-pyrido[1,2-a]pyrimidine chloride and 5 mmoles of sodium acetate in 5 ml. of anhydrous ethanol is allowed to stand for 24 hours at room temperature and the precipitated sodium chloride is filtered and the filtrate is evaporated. The residue is dissolved in water and the pH of the solution is adjusted to 7 by adding sodium hydrogen carbonate. The precipitated crystals are filtered, washed with water and dried. 0.92 g. (60%) of 3,9-diethoxycarbonyl-6-methyl-4-oxo-1,6,7,8-tetrahydro-4H-pyrido[1,2-a]pyrimidine is obtained, melting point: 138°–140° C.

Analysis: for the formula $C_{15}H_{20}N_2O_5$; calculated: C: 58.43%; H: 6.54%; N: 9.09%; found: C: 58.65%; H: 6.53%; N: 9.06%.

EXAMPLE 7

A solution of 1.8 g. of 3-ethoxycarbonyl-6-methyl-9-[(chloro-N,N-dimethyl-ammonio)-methylene]-4-oxo-6,7,8,9-tetrahydro-4H-pyrido[1,2-a]pyrimidine chloride and 5 mmoles of sodium acetate in 5 ml. of anhydrous methanol is allowed to stand for 24 hours at room temperature and the precipitated sodium chloride is filtered and the filtrate is evaporated. The residue is dissolved in water and the pH of the solution is adjusted to 7 by adding sodium carbonate. The precipitated crystals are filtered and washed with water and dried.

0.96 g. (65%) of 3-ethoxycarbonyl-6-methyl-9-methoxycarbonyl-4-oxo-1,6,7,8-tetrahydro-4H-pyrido[1,2-a]pyrimidine is obtained which melts at 136°–139° C.

Analysis: for the formula $C_{14}H_{18}N_2O_5$; calculated: C: 57.14%; H: 6.17%; N: 9.52%; found: C: 57.00%; H: 6.25%; N: 9.52%.

EXAMPLES 8 to 13

To a solution of 3.65 g. of 3-ethoxycarbonyl-6-methyl-9-[(chloro-N,N-dimethyl-ammonio)-methylene]-4-oxo-6,7,8,9-tetrahydro-4H-pyrido[1,2-a]pyrimidine chloride in 15 ml. of anhydrous dichloromethane 0.02 mole of amine is added and the reaction mixture is stirred for 1 hour. After cooling the precipitated amine hydrochloride is filtered. The filtrate is evaporated. The oily, crystallizing residue is crystallized with ether. The obtained crystals are filtered, washed with ether and dried. The product is recrystallized from anhydrous ethanol. The obtained substances and data thereof are shown in Table 1.

TABLE 1

| Example No. | Amine | Product | Yield % | Mp. °C. | Empirical formula | Analysis calculated / found | | |
|---|---|---|---|---|---|---|---|---|
| | | | | | | C % | H % | N % |
| 8 | aniline | 3-ethoxycarbonyl-6-methyl-9-(N-phenyl-N',N'-dimethyl-formamidinium)-4-oxo-1,6,7,8-tetrahydro-4H-pyrido[1,2-a]-pyrimidine-chloride | 74 | 236–239 (decomp.) | $C_{21}H_{27}N_4O_3Cl$ | 60.30 60.08 | 6.45 6.54 | 13.40 13.42 |
| 9 | 4-chloro-aniline | 3-ethoxycarbonyl-6-methyl-9-[N-(4-chloro-phenyl)-N',N'-dimethyl-formamidinium]-4-oxo-1,6,7,8-tetrahydro-4H-pyrido[1,2-a]pyrimidine chloride | 75 | 230–232 (decomp.) | $C_{21}H_{26}N_4O_3Cl_2$ | 55.60 54.95 | 5.74 5.73 | 12.35 12.26 |
| 10 | 4-methyl-aniline | 3-ethoxycarbonyl-6-methyl-9-[N-(4-methyl-phenyl)-N',N'-dimethyl-formamidinium]-4-oxo-1,6,7,8-tetrahydro-4H-pyrido[1,2-a]pyrimidine chloride | 81 | 225–226 (decomp.) | $C_{22}H_{29}N_4O_3Cl$ | 61.10 60.83 | 6.70 6.81 | 12.92 12.79 |
| 11 | 4-methoxy-aniline | 3-ethoxycarbonyl-6-methyl-9-[N-(4-methoxy-phenyl)-N',N'-dimethyl-formamidinium]-4-oxo-1,6,7,8-tetrahydro-4H-pyrido[1,2-a]pyrimidine chloride | 38 | 222–224 (decomp.) | $C_{22}H_{29}N_4O_4Cl$ | 58.95 58.58 | 6.47 6.65 | 12.50 12.58 |
| 12 | 2-naphtyl-amine | 3-ethoxycarbonyl-6-methyl-9-[N-(2-naphtyl)-N',N'-dimethyl-formamidinium]-4-oxo-1,6,7,8-tetrahydro-4H-pyrido[1,2-a]pyrimidine chloride | 68 | 234–235 | $C_{25}H_{29}N_4O_3Cl$ | 64.10 63.69 | 6.19 6.17 | 11.95 11.82 |
| 13 | 2-methoxy-carbonyl-aniline | 3-ethoxycarbonyl-6-methyl-9-[N-(2-methoxy-carbonyl-phenyl)-N',N'-dimethyl-formamidinium]-4-oxo-1,6,7,8-tetrahydro-4H-pyrido[1,2-a]pyrimidine chloride | 63 | 210–211 (decomp.) | $C_{23}H_{29}N_4O_5Cl$ | 57.91 57.33 | 6.09 6.09 | 11.75 11.76 |

EXAMPLE 14

To an aqueous solution of 4.2 g. of 3-ethoxycarbonyl-6-methyl-9-(N-phenyl-N',N'-dimethyl-formamidinium)-4-oxo-1,6,7,8-tetrahydro-4H-pyrido[1,2-a]pyrimidine chloride a 20 by % W/V solution of potassium carbonate is added. The precipitated crystals are filtered, washed with water and dried.

3.4 g. (89%) of 3-ethoxycarbonyl-6-methyl-9-(N-phenyl-N',N'-dimethyl-formamidino)-4-oxo-1,6,7,8-tetrahydro-4H-pyrido[1,2-a]pyrimidine is obtained which after recrystallization from ethanol melts at 193°–195° C.

Analysis: for the formula $C_{21}H_{26}N_4O_3$; calculated: C: 65.98%; H: 6.81%; N: 14.65%; found: C: 65.89%; H: 6.79%; N: 14.69%.

EXAMPLE 15

To a mixture of 22.1 g. of phosgene-N-methyl-N-phenyl-immonium chloride in 50 ml. of dichloromethane 23.6 g. of 3-ethoxycarbonyl-6-methyl-4-oxo-6,7,8,9-tetrahydro-4H-pyrido[1,2-a]pyrimidine in 30 ml. of dichloromethane is added dropwise and the reaction mixture is boiled for 3 hours. The solvent is distilled off and the residue is crystallized with ether. 41.2 g of highly hygroscopic 3-ethoxycarbonyl-6-methyl-9-[(chloro-N-methyl-N-phenyl-ammonio)-methylene]-4-oxo-6,7,8,9-tetrahydro-4H-pyrido[1,2-a]pyrimidine chloride is obtained and dried in vacuo.

Analysis: for the formula $C_{20}H_{23}N_3O_3Cl_2$; calculated: $Cl_{ionic}$: 8.36%; found: $Cl_{ionic}$: 8.45%.

EXAMPLE 16

To a solution of 21 g. of 3-ethoxycarbonyl-6-methyl-9-[(chloro-N-methyl-N-phenyl-ammonio)-methylene]4-oxo-6,7,8,9-tetrahydro-4H-pyrido[1,2-a]pyrimidine chloride in 20 ml. of anhydrous dichloromethane 0.2 mole of aniline is added and the reaction mixture is boiled for 1 hour. After cooling the precipitated aniline hydrochloride is filtered. The dichloromethane mother-liquor is evaporated. The residue is crystallized from ether. The precipitated crystals are filtered, washed with ether and dried. 25.9 g. (54%) of 3-ethoxycarbonyl-6-methyl-9-(N',N'-diphenyl-N-methyl-formamidinium)-4-oxo-1,6,7,8-tetrahydro-4H-pyrido[1,2-a]pyrimidine chloride is obtained, which melts at 186°–188° C. under decomposition after recrystallization from ethanol.

Analysis: for the formula $C_{26}H_{29}N_4O_3Cl$; calculated: C: 64.95%; H: 6.04%; N: 11.66%; found: C: 64.76%; H: 6.09%; N: 11.26%.

EXAMPLE 17

To an aqueous solution of 24 g. of 3-ethoxycarbonyl-6-methyl-9-(N,N'-diphenyl-N-methyl-formamidinium)-4-oxo-1,6,7,8-tetrahydro-4H-pyrido[1,2-a]pyrimidine chloride a 20% by W/V solution of potassium carbonate is added dropwise. The precipitated crystals are filtered and washed with water and dried. 16.7 g. (75%) of 3-ethoxycarbonyl-6-methyl-9-(N,N'-diphenyl-N-methyl-formamidino)-4-oxo-1,6,7,8-tetrahydro-4H-pyrido[1,2-a]pyrimidine is obtained, which after recrystallization from ethanol melts at 199°–202° C.

Analysis: for the formula $C_{26}H_{28}N_4O_3$; calculated: C: 70.25%; H: 6.31%; N: 12.61%; found: C: 69.97%; H: 6.27%; N: 12.42%.

EXAMPLE 18

To a solution of 21 g. of 3-ethoxycarbonyl-6-methyl-9-[(chloro-N-methyl-N-phenyl-ammonio)-methylene]-4-oxo-6,7,8,9-tetrahydro-4H-pyrido[1,2-a]pyrimidine chloride in 20 ml. of anhydrous dichloromethane 0.2 mole of 4-chloro-aniline is added and the reaction mixture is boiled for 1 hour. The 4-chloro-anilinehydrochloride precipitated after cooling is filtered. The dichloromethane mother liquor is evaporated. The obtained 3-ethoxycarbonyl-6-methyl-9-[N-(4-chloro-phenyl)-N'-methyl-formamidinium]-4-oxo-1,6,7,8-tetrahydro-4H-pyrido[1,2-a]pyrimidine chloride is dissolved in water and to the solution a 20% by W/V solution of potassium carbonate is added. The precipitated crystals are filtered, washed with water and dried. 13.3 g. (55.5%) of 3-ethoxycarbonyl-6-methyl-9-[N-(4-chloro-phenyl)-N'-phenyl-N'-methyl-formamidino]-4-oxo-1,6,7,8-tetrahydro-4H-pyrido[1,2-a]pyrimidine is obtained, which melts at 194°–196° C. after recrystallization from ethanol.

Analysis: for the formula $C_{26}H_{27}N_4O_3Cl$; calculated: C: 65.15%; H: 5.65%; N: 11.71%; found: C: 64.85%; H: 5.83%; N: 11.66%.

EXAMPLE 19

To 21 g. of 3-ethoxycarbonyl-6-methyl-9-[(chloro-N-methyl-N-phenyl-ammonio)-methylene]-4-oxo-6,7,8,9-tetrahydro-4H-pyrido[1,2-a]pyrimidine chloride dissolved in 20 ml. of anhydrous dichloromethane 0.2 mole of 4-methyl-aniline is added and the reaction mixture is stirred for 1 hour. After cooling the precipitated 4-methyl-aniline-hydrochloride is filtered. The dichloromethane filtrate is evaporated. The obtained 3-ethoxycarbonyl-6-methyl-9-[N'-(4-methyl-phenyl)-N'-phenyl-N'-]methyl-formamidinium]-4-oxo-1,6,7,8-tetrahydro-4H-pyrido-[1,2-a]pyrimidine chloride is dissolved in water. To the aqueous solution 20% by W/V solution of potassium carbonate is added. The precipitated crystals are filtered, washed with water and dried.

14.7 g. (64%) of 3-ethoxycarbonyl-6-methyl-9-[N'-(4-methyl-phenyl)-N'-phenyl-N'-methyl-formamidino]-4-oxo-1,6,7,8-tetrahydro-4H-pyrido[1,2-a]pyrimidine is obtained, which after recrystallization from ethanol melts at 161°–163° C.

Analysis: for the formula $C_{27}H_{30}N_4O_3$; calculated: C: 70.75%; H: 6.56%; N: 12.21%; found: C: 70.35%; H: 6.62%; N: 11.91%.

EXAMPLES 20 TO 23

To a dichloromethane solution of 0.05 mole of a nitrogen bridgehead compound 0.055 mole of isocyanate is added dropwise at room temperature and the reaction mixture is heated for 10 hours and allowed to stand for 2 days, whereafter the solvent is distilled off. The residue is crystallized from ethanol. The prepared products are shown in Table 2.

TABLE 2

| Example No. | Starting material | Isocyanate | Product | Yield % | Mp. °C. | Empirical formula | Analysis calculated found | | |
|---|---|---|---|---|---|---|---|---|---|
| | | | | | | | C % | H % | N % |
| 20 | 3-ethoxycarbonyl-6-methyl-4-oxo-6,7,8,9-tetra- | phenyl-iso- | 3-ethoxycarbonyl-6-methyl-9-[N-phenyl-amino-carbonyl]-4- | 46 | 200–201 | $C_{19}H_{21}N_3O_4$ | 64.21 | 5.95 | 11.83 |

TABLE 2-continued

| Example No. | Starting material | Isocyanate | Product | Yield % | Mp. °C. | Empirical formula | Analysis calculated found | | |
|---|---|---|---|---|---|---|---|---|---|
| | | | | | | | C % | H % | N % |
| | hydro-4H-pyrido-[1,2-a]pyrimidine | cyanate | oxo-1,6,7,8-tetra-hydro-4H-pyrido-[1,2-a]pyrimidine | | | | 63.95 | 5.81 | 11.65 |
| 21 | 3-ethoxycarbonyl-6-methyl-4-oxo-6,7,8,9-tetra-hydro-4H-pyrido-[1,2-a]pyrimidine | chloro-acetyl-iso-cyanate | 3-ethoxycarbonyl-6-methyl-9-(chloro-acetyl-amino-carbonyl)-4-oxo-1,6,7,8-tetrahydro-4H-pyrido[1,2-a]pyrimidine | 74 | 158–160 | $C_{15}H_{18}N_3O_5Cl$ | 50.63 | 5.06 | 11.80 |
| 22 | 3-ethoxycarbonyl-6-methyl-4-oxo-6,7,8,9-tetra-hydro-4H-pyrido-[1,2-a]pyrimidine | tosyl-isocyana-te | 3-ethoxycarbonyl-6-methyl-9-(tosyl-amino-carbonyl)-4-oxo-1,6,7,8-tetra-hydro-4H-pyrido-[1,2-a]pyrimidine | 80 | 182–183 | $C_{20}H_{23}N_3O_6S$ | 55.42 55.92 | 5.35 5.30 | 9.69 9.72 |
| 23 | 3-aminocarbonyl-6-methyl-4-oxo-6,7,8,9-tetra-hydro-4H-pyrido-[1,2-a]pyrimidine | tosyl-iso-cyanate | 3-[(tosylamino-carbonyl)-aminocarbonyl]-6-methyl-9-(tosyl-amino-carbonyl)-4-oxo-1,6,7,8-tetrahydro-4H-pyrido[1,2-a]pyrimidine | 49 | 164 | $C_5H_6N_4O_7S_2$ | 51.90 52.28 | 4.52 4.48 | 11.64 11.51 |

EXAMPLES 24 TO 28

A mixture of 23.6 g. of 3-ethoxycarbonyl-6-methyl-4-oxo-4H-pyrido[1,2-a]pyrimidine and 0.1 mole of isocyanate is stirred for 72 hours at 40°–50° C. The formed thick viscous reaction mixture is suspended in 200 ml. of ethanol, filtered and washed with ethanol (when using n-butyl-isocyanate the reaction is carried out at 80°–100° C.). The prepared compounds are shown in Table 3.

1.08 g. (63%) of 3-ethoxycarbonyl-6-methyl-9-(N,N-dimethylamino-carbonyl)-4-oxo-6,7,8,9-tetrahydro-4H-pyrido[1,2-a]pyrimidine hydrochloride is obtained, which after recrystallization from ethanol metls at 166°–168° C. (decomposition).

Analysis: for the formula $C_{15}H_{22}N_3O_4Cl$; calculated: C: 52.40%; H: 6.45%; N: 12.22%; Cl: 10.31%; found: C: 52.18%; H: 6.58%; N: 12.30%; Cl: 10.45%.

TABLE 3

| Example No. | Isocyanate | Product | Yield % | Mp. °C. | Empirical formula | Analysis calculated found | | |
|---|---|---|---|---|---|---|---|---|
| | | | | | | C % | H % | N % |
| 24 | n-butyl-iso-cyanate | 3-ethoxycarbonyl-6-methyl-9-[(n-butylamino)-carbonyl]-4-oxo-1,6,7,8-tetrahydro-4H-pyrido[1,2-a]pyrimidine | 35 | 152–155 | $C_{17}H_{25}N_3O_4$ | 60.90 60.25 | 7.47 7.41 | 12.52 12.40 |
| 25 | phenyl-iso-cyanate | 3-ethoxycarbonyl-6-methyl-9-[(phenyl-amino)-carbonyl]-4-oxo-1,6,7,8-tetrahydro-4H-pyrido[1,2-a]pyrimidine | 74 | 198–200 | $C_{19}H_{21}N_3O_4$ | No melting point depression with the product of Example 20 | | |
| 26 | 4-chloro-phenyl-iso-cyanate | 3-ethoxycarbonyl-6-methyl-9-[(4-chloro-phenyl-amino)-carbonyl]-4-oxo1,6,7,8-tetrahydro-4H-pyrido[1,2-a]-pyrimidine | 82 | 206–210 | $C_{19}H_{20}N_3O_4Cl$ | 58.50 58.10 | 5.13 5.07 | 10.78 10.59 |
| 27 | 3-chloro-phenyl-iso-cyanate | 3-ethoxycarbonyl-6-methyl-9-[(3-chloro-phenyl-amino]-carbonyl/-4-oxo-1,6,7,8-tetrahydri-4H-pyrido[1,2-a]-pyrimidine | 78 | 194–198 | $C_{19}H_{20}N_3O_4Cl$ | 58.50 58.21 | 5.13 5.05 | 10.78 10.61 |
| 28 | 3,4-di-chloro-phenyl-iso-cyanate | 3-ethoxycarbonyl-6-methyl-9-[(3,4-dichloro- henyl-amino)-carbonyl]-4-oxo-1,6,7,8-tetrahydro-4H-pyrido[1,2-a]pyrimidine | 79 | 208 212 | $C_{19}H_{19}N_3O_4Cl_2$ | 53.80 53.28 | 4.48 4.40 | 9.90 9.78 |

EXAMPLE 29

A solution of 1.8 g. of 3-ethoxycarbonyl-6-methyl-9-[(chloro-N,N-dimethyl-ammonio)-methylene]-4-oxo-6,7,8,9-tetrahydro-4H-pyrido[1,2-a]pyrimidine chloride in 5 ml. of ethanol is boiled for 30 minutes. The crystals are precipitated after cooling, filtered, washed with ethanol and dried.

EXAMPLE 30

3.26 g. of 3-ethoxycarbonyl-6-methyl-9-(methylthio-thiocarbonyl)-4-oxo-1,6,7,8-tetrahydro-4H-pyrido[1,2-a]-pyrimidine and 0.6 g. of ethylene diamine are boiled in 50 ml. of benzene for 10 hours. The precipitated yellow crystals are filtered, covered with benzene and dried.

1.9 g. (62%) of 3-ethoxycarbonyl-6-methyl-9-(2-imidazolidene)-4-oxo-6,7,8,9-tetrahydro-4H-pyrido[1,2- a]pyrimidine are obtained, which melts at 252°–254° C. after recrystallization from dimethylformamide.

Analysis: for the formula $C_{15}H_{18}N_4O_3$; calculated: C: 59.15%; H: 5.90%; N: 18.40%; found: C: 58.91%; H: 5.85%; N: 18.35%.

EXAMPLE 31

1.0 g. of 3-ethoxycarbonyl-6-methyl-9-(2-imidazolidene)-4-oxo-6,7,8,9-tetrahydro-4H-pyrido[1,2-a]-pyrimidine is dissolved in 10 ml. of ethanol and the solution is saturated with hydrogenchloride gas and evaporated. The residue is recrystallized from a mixture of ethanol and ether.

0.9 g. of 3-ethoxycarbonyl-6-methyl-9-(2-imidazolidene)-4-oxo-6,7,8,9-tetrahydro-4H-pyrido[1,2-a]pyrimidine-bis hydrochloride is obtained, melting under decomposition at 190° C.

Analysis: for the formula $C_{15}H_{20}N_4O_3Cl_2$; calculated: C: 48.01%; H: 5.37%; N: 14.93%; Cl: 18.90%; found: C: 47.82%; H: 5.18%; N: 15.06%; Cl: 19.01%.

EXAMPLE 32

3.6 g. of 3-ethoxycarbonyl-6-methyl-9-[(chloro-N,N-dimethylammonio)-methylene]-4-oxo-6,7,8,9-tetrahydro-4H-pyrido[1,2-a]pyrimidine chloride are stirred with 1.2 g. of ethylenediamine in 40 ml. of dimethylformamide at 40° C. for 2 hours and after cooling the precipitated crystals are filtered, washed with water and dried. 1.0 g. of 3-ethoxycarbonyl-6-methyl-9-(2-imidazolidene)-4-oxo-6,7,8,9-tetrahydro-4H-pyrido[1,2-a]pyrimidine is obtained, which melts at 252°–254° C.

EXAMPLE 33

A mixture of 2.0 g. of 3-amino-carbonyl-2,6-dimethyl-4-oxo-6,7,8,9-tetrahydro-4H-pyrido[1,2-a]pyrimidine and 2.2 g. of phenyl isocyanate is heated to 80° C. and the obtained solution is stirred for 10 hours at 40°–60° C. After cooling the reaction mixture is treated with ether and the precipitated crystals are filtered, washed with ether and dried. The obtained crystals are dissolved in ethanol, filtered and the filtrated is placed to a refrigerator and allowed to crystallize. The precipitated crystals are filtered, washed with ethanol.

1.4 g. of 3-amino-carbonyl-9-(phenylamino-carbonyl)-2,6-dimethyl-4-oxo-1,6,7,8-tetrahydro-4H-pyrido[1,2-a]pyrimidine is obtained, melting point: 187°–188° C.

Analysis: for the formula $C_{18}H_{20}N_4O_3$; calculated: C: 63.51%; H: 5.92%; N: 16.46%; found: C: 63.49%; H: 6.00%; N: 16.26%.

EXAMPLE 34

1.6 g. of potassium hydroxide is dissolved in 20 ml. of ethanol. To this solution 3.6 g. 3-ethoxycarbonyl-9-(phenylamino-carbonyl)-6-methyl-4-oxo-1,6,7,8-tetrahydro-4H-pyrido[1,2-a]pyrimidine dissolved in ethanol is added. The reaction mixture is boiled for 30 minutes and the crystals precipitated after cooling are filtered, washed with chloroform and dried.

3.1 g. of potassium salt of 9-(phenylamino-carbonyl)-6-methyl-4-oxo-1,6,7,8-tetrahydro-4H-pyrido[1,2-a]pyrimidine-3-carboxylate is obtained which is decomposed at 276°–280° C.

Analysis: for the formula $C_{17}H_{16}N_3O_4K$; calculated: C: 55.88%; H: 4.41%; N: 11.50%; found: C: 56.02%; H: 4.50%; N: 11.42%.

EXAMPLE 35

3.1 g. of potassium salt of 9-(phenyl-aminocarbonyl)-6-methyl-4-oxo-1,6,7,8-tetrahydro-4H-pyrido-[1,2-a]pyrimidine-3-carboxylate are dissolved in 250 ml. of water under heating. The pH of the solution is adjusted to 1 at 40°–50° C. by adding an about 38% by W/V solution of hydrochloric acid. The crystals precipitated upon cooling are filtered, washed with water and dried. The obtained 2.2 g. of product is crystallized from acetonitrile.

Thus 9-(phenyl-amino-carbonyl)-3-carboxy-6-methyl-4-oxo-1,6,7,8-tetrahydro-4H-pyrido[1,2-a]pyrimidine is obtained, melting point: 200°–201° C. Yield: 25%.

Analysis: for the formula $C_{17}H_{17}N_3O_4$; calculated: C: 62.37%; H: 5.24%; N: 12.84%; found: C: 62.18%; H: 5.18%; N: 12.45%.

EXAMPLE 36

2 g. of 6-methyl-4-oxo-6,7,8,9-tetrahydro-4H-pyrido[1,2-a]pyrimidine are reacted with phosgene-N,N-dimethyl-immonium chloride as described in Example 5. Thus highly hygroscopic 6-methyl-9-[(chloro-N,N-dimethyl-ammonio)-methylene]-4-oxo-6,7,8,9-tetrahydro-4H-pyrido[1,2-a]pyrimidine chloride is obtained, which is dried in vacuo.

Analysis: for the formula $C_{12}H_{17}N_3OCl_2$; calculated: $Cl_{ionic}$: 12.22%; found: $Cl_{ionic}$: 12.10%.

EXAMPLE 37

6-Methyl-9-[(chloro-N,N-dimethylammonio)-methylene]-4-oxo-6,7,8,9-tetrahydro-4H-pyrido[1,2-a]pyrimidine chloride is boiled for 30 minutes in ethanol. The reaction mixture is evaporated and the obtained 6-methyl-9-(N,N-dimethylamino-carbonyl)-4-oxo-6,7,8,9-tetrahydro-4H-pyrido[1,2-a]pyrimidine hydrochloride is converted to base by conventional methods. The base is crystallized from petrolether.

Thus 6-methyl-9-(N,N-dimethylamino-carbonyl)-4-oxo-1,6,7,8-tetrahydro-4H-pyrido[1,2-a]pyrimidine is obtained, melting point: 78° C.

Analysis: for the formula $C_{12}H_{17}N_3O_2$; calculated: C: 61.26%; H: 7.28%; N: 17.86%; found: C: 61.40%; H: 7.11%; N: 17.69%.

EXAMPLE 38

3-Cyano-6-methyl-4-oxo-6,7,8,9-tetrahydro-4H-pyrido[1,2-a]pyrimidine is reacted as described in Example 5 with phosgene-N,N-dimethyl-immonium chloride. Thus highly hygroscopic 3-cyano-6-methyl-9-[(chloro-N,N-dimethyl-ammonio)-methylene]-4-oxo-6,7,8,9-tetrahydro-4H-pyrido[1,2-a]pyrimidine chloride is obtained Analysis: for the formula $C_{13}H_{16}N_4OCl_2$; calculated: $Cl_{ionic}$: 10.70%; found: $Cl_{ionic}$ I 10.52%.

EXAMPLE 39

3-Cyano-6-methyl-9-[(chloro-N,N-dimethyl-ammonio)methylene]-4-oxo-6,7,8,9-tetrahydro-4H-pyrido[1,2-a]pyrimidine chloride is treated as given in Example 29. The ethanol solution is evaporated and the obtained residue is crystallized from ethyl acetate. Thus 3-cyano-6-methyl-9-(N,N-dimethylamino-carbonyl)-4-oxo-1,6,7,8-tetrahydro-4H-pyrido[1,2-a]pyrimidine is obtained, yield: 60%.

Analysis: for the formula $C_{13}H_{16}N_4O_2$; calculated: C: 59.98%; H: 6.20%; N: 21.51%; found: C: 59.90%; H: 6.11%; N: 21.22%.

EXAMPLE 40

3.4 g. of 3-ethoxycarbonyl-6-methyl-9-(N,N-dimethylamino-carbonyl)-4-oxo-6,7,8,9-tetrahydro-4H-pyrido[1,2-a]pyrimidine hydrochloride are dissolved in 20 ml. of water and the solution is neutralized with a 5% by W/V solution of sodium hydrogen carbonate. The reaction mixture is shaken out with chloroform. The chloroform solution is dried above sodium sulfate, filtered and evaporated. The residue is crystallized from a mixture of ethanol and water.

2.1 g. of 3-ethoxycarbonyl-6-methyl-9-(N,N-dimethylamino-carbonyl)-4-oxo-1,6,7,8-tetrahydro-4H-pyrido[1,2-a]pyrimidine is obtained.

Analysis: for the formula $C_{15}H_{21}N_3O_4$; calculated: C: 58.60%; H: 6.90%; N: 13.66%; found: C: 58.25%; H: 6.94%; N: 13.56%.

EXAMPLE 41

3.07 g. of 3-ethoxycarbonyl-6-methyl-9-(N,N-dimethylamino-carbonyl)-4-oxo-1,6,7,8-tetrahydro-4H-pyrido[1,2-a]pyrimidine are dissolved in ethanol. To the solution a 20% by W/V solution of ammonia in ethanol is added and the reaction mixture is allowed to stand in a closed vessel at room temperature for 3 days. The precipitated crystals are filtered, washed with ethanol. 1.18 g. of 3-aminocarbonyl-6-methyl-9-(N,N-dimethylamino-carbonyl)-4-oxo-1,6,7,8-tetrahydro-4H-pyrido[1,2-a]pyrimidine is obtained, melting point 220° C.

Analysis: for the formula $C_{13}H_{18}N_4O_3$; calculated: C: 56.09%; H: 6.53%; N: 20.12%; found: C: 55.89%; H: 6.52%; N: 20.33%.

EXAMPLE 42

3,6-Diethoxycarbonyl-6-methyl-4-oxo-1,6,7,8-tetrahydro-4H-pyrido[1,2-a]pyrimidine is treated with ethanolic ammonia as disclosed in Example 41. 1.51 g. of 3-aminocarbonyl-9-ethoxycarbonyl-6-methyl-4-oxo-1,6,7,8-tetrahydro-4H-pyrido[1,2-a]pyrimidine is obtained, melting point: 251° C.

Analysis: for the formula $C_{13}H_{17}N_3O_4$; calculated: C: 57.12%; H: 6.28%; N: 15.30%; found: C: 56.98%; H: 6.12%; N: 15.50%.

EXAMPLE 43

0.416 g. of 3-ethoxycarbonyl-4-oxo-4,6,7,8-tetrahydro-pyrrolo[1,2-a]pyrimidine is dissolved in 4 ml. of benzene and to the solution 0.24 g. of phenylisocyanate is added. The reaction mixture is allowed to stand for 5 days at room temperature and the precipitated crystals are filtered and washed with benzene.

0.50 g. (76.5%) of 3-ethoxycarbonyl-8-(N-phenyl-aminocarbonyl)-4-oxo-1,4,6,7-tetrahydro-pyrrolo[1,2-a]pyrimidine is obtained, melting point: 240°–241° C.

Analysis: for the formula $C_{17}H_{17}N_3O_4$; calculated: C: 62.38%; H: 5.23%; N: 12.84%; found: C: 62.51%; H: 5.15%; N: 12.90%.

EXAMPLE 44

0.8 g. of 3-cyano-4-oxo-4,6,7,8-tetrahydro-pyrrolo[1,2-a]pyrimidine and 0.6 ml. of carbon disulfide are dissolved in 10 ml. of ethanol and to the solution 0.6 g. of potassium hydroxide in 10 ml. of ethanol is added dropwise. The reaction mixture is stirred for 1 hour at room temperature and evaporated at reduced pressure. Thus 3-cyano-8-[(bis-thiolate)-methylene]-4-oxo-4,6,7,8-tetrahydro-pyrrolo[1,2-a]pyrimidine dipotassium salt is obtained.

EXAMPLE 45

3-Cyano-9-[(bis-thiolat)-methylene]-4-oxo-4,6,7,8-tetrahydro-pyrrolo[1,2-a]pyrimidine dipotassium salt as prepared according to Example 44 is dissolved in 20 ml. of ethanol and to the solution 1.25 g. dimethylsulfate is added and the reaction mixture is stirred for 1 hour at 40° C. The precipitated crystals are filtered, washed with ethanol.

0.46 g. (36.5%) of 3-cyano-9-(methylthio-thiocarbonyl)4-oxo-1,4,6,7-tetrahydro-pyrrolo[1,2-a]pyrimidine is obtained, which melts at 202°–3° C.

Analysis: for the formula $C_{10}H_9N_3OS_2$; calculated: C: 47.79%; H: 3.61%; N: 16.72%; found: C: 48.01%; H: 3.52%; N: 16.81%.

EXAMPLE 46

To 0.66 g. of an oily 80% sodium hydride suspension 50 ml. of benzene are added, whereafter 4.72 g. of 3-ethoxycarbonyl-6-methyl-4-oxo-6,7,8,9-tetrahydro-4H-pyrido[1,2-a]-pyrimidine dissolved in 15 ml. of benzene are added dropwise. After stirring for 30 minutes a solution of 2.96 g. of methyl thioisocyanate in 10 ml. of benzene is added within 10 minutes at a temperature of 25° to 35° C. The mixture is stirred for 2 hours and by adding 80 ml. of ether the sodium salt of the formed 3-ethoxycarbonyl-6-methyl-9-(methylamino-thiocarbonyl)-4-oxo-6,7,8,9-tetrahydro-4H-pyrido[1,2-a]pyrimidine is precipitated in an oily form. The solvent is discarded and the residue is triturated with ether and dried in a vacuum desiccator. Thus 5.3 g. (80%) of the amorphous 3-ethoxycarbonyl-6-methyl-9-(methylamino-thiocarbonyl)-4-oxo-6,7,8,9-tetrahydro-4H-pyrido[1,2-a]pyrimidine are obtained in the form of a sodium salt.

EXAMPLE 47

To the sodium salt of the 3-ethoxycarbonyl-6-methyl-9-(methylamino-thiocarbonyl)-4-oxo-6,7,8,9-tetrahydro-4H-pyrido[1,2-a]pyrimidine obtained by the process of Example 46, 15 ml. of acetone and 130 ml. of water are added, the pH value of the solution is thereafter adjusted to 3–4 by the addition of acetic acid. The precipitated crystals are filtered, washed with water and dried, recrystallized from ethyl alcohol. Thus 3.2 g. of the 3-ethoxycarbonyl-6-methyl-9-(methylamino-thiocarbonyl)-4-oxo-6,7,8,9-tetrahydro-4H-pyrido[1,2-a]pyrimidine are obtained, melting at 199° to 200° C. Yield: 52%.

Analysis based on the formula $C_{14}H_{19}N_3O_3S$: Calculated: C 54.35% H 6.19% N 13.58%; Found: C 54.45% H 6.18% N 13.72%.

EXAMPLE 48

To 0.66 g. of an oily 80% sodium hydride suspension 50 ml. of benzene are added, whereafter 4.72 g. of 3-ethoxycarbonyl-6-methyl-4-oxo-6,7,8,9-tetrahydro-4H-pyrido[1,2-a]pyrimidine dissolved in 15 ml. of benzene are added dropwise. After stirring for 30 minutes 5.4 g. of phenyl thioisocyanate dissolved in 10 ml. of benzene is added within 10 minutes at a temperature of 25°–35° C. The mixture is stirred for 2 hours and by adding 80 ml. of ether the sodium salt of the formed 3-ethoxycarbonyl-6-methyl-9-(phenylamino--thiocarbonyl)-4-oxo-6,7,8,9-tetrahydro-4H-pyrido[1,2- a]pyrimidine is precipitated in an oily form. The solvent is discarded and the residue is triturated with ether and the product is dried in a vacuum desiccator. Thus 6.1 g. (76%) of the amorphous sodium salt of the 3-ethoxycarbonyl-6-methyl-9-(phenylamino-thiocarbonyl)-4-oxo-6,7,8,9-tetrahydro-4H-pyrido[1,2-a]pyrimidine are obtained.

EXAMPLE 49

To the sodium salt of the 3-ethoxycarbonyl-6-methyl-9-(phenylamino-thiocarbonyl)-4-oxo-6,7,8,9-tetrahydro-4H-pyrido[1,2-a]pyrimidine obtained according to the process of Example 48. 15 ml. of acetone and 130 ml. of water are added, whereafter the pH value of the solution obtained is adjusted to 3-4 by the addition of acetic acid. The precipitated crystals are filtered, washed with water and dried, recrystallized from acetonitrile. Thus 3.2 g. (52%) of the 3-ethoxycarbonyl-6-methyl-9-(phenylaminothiocarbonyl)-4-oxo-1,6,7,8-tetrahydro-4H-pyrido[1,2-a]pyrimidine are obtained, melting at 173°-175° C.

Analysis based on the formula $C_{19}H_{21}N_3O_3S$: Calculated: C 61.44% H 5.70% N 11.31%; Found: C 61.75% H 5.57% N 11.40%.

What we claim is:
1. A compound of the formula (I')

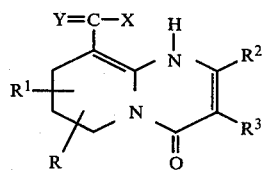

or a tautomer, optically active antipode, or pharmaceutically acceptable salt thereof wherein R, $R^1$ and $R^2$ are each hydrogen or $C_1$ to $C_4$ alkyl;

$R^3$ is carboxy, $C_1$ to $C_6$ alkoxycarbonyl, carbamoyl, cyano, —CONH—$SO_2$—$C_6H_4$—p—$CH_3$ or —$(CH_2)_s$—COO$R^{14}$ wherein s is 1, 2 or 3 and $R^{14}$ is hydrogen or $C_1$ to $C_4$ alkyl;

X is halogen, —O$R^4{}_1$, —S$R^4{}_1$ wherein $R^4{}_1$ is hydrogen or $C_1$ to $C_4$ alkyl, or X is —N($R^4$)($R^5$) wherein $R^4$ is chloroacetyl, $C_1$ to $C_4$ alkyl, tosyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen;

$R^5$ is hydrogen or $C_1$ to $C_4$ alkyl; and

Y is oxygen, sulfur, or =N—$R^7$ wherein $R^7$ is $C_1$ to $C_4$ alkyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen.

2. A compound of the formula (I")

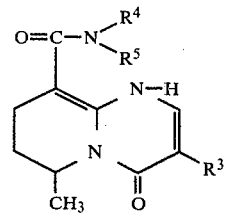

or a tautomer, optically active antipode or pharmaceutically acceptable salt thereof wherein $R^3$ is hydrogen, $C_1$ to $C_4$ alkyl, phenyl, carboxy, $C_1$ to $C_6$ alkoxycarbonyl, carbamoyl, cyano, —CONH—$SO_2$—$C_6H_4$—p—$CH_3$ or —$(CH_2)_5$—COO$R^{14}$ wherein s is 1, 2 or 3 and $R^{14}$ is hydrogen or $C_1$ to $C_4$ alkyl;

$R^4$ is chloroacetyl, $C_1$ to $C_4$ alkyl, tosyl, phenyl, naphthyl, or phenyl or naphthyl substituted by $C_1$ to $C_4$ alkyl, $C_1$ to $C_4$ alkoxy, amino, hydroxy, carboxy, $C_1$ to $C_4$ alkoxycarbonyl, nitrile, carbamoyl, carbohydrazido, nitro or halogen; and $R^5$ is hydrogen or $C_1$ to $C_4$ alkyl.

3. A compound as defined in claim 1 which is:
3-ethoxycarbonyl-6-methyl-9-[N-phenylamino-carbonyl]-4-oxo-1, 6,7,8-tetrahydro-4H-pyrido[1,2-a]pyrimidine;

3-ethoxycarbonyl-6-methyl-9-(chloroacetyl-amino-carbonyl)-4-oxo-1,6,7,8-tetrahydro-4H-pyrido[1,2-a]pyrimidine;

3-ethoxycarbonyl-6-methyl-9-(tosyl-amino-carbonyl)-4-oxo-1, 6,7,8-tetrahydro-4H-pyrido[1,2-a]pyrimidine;

3-(tosylamino-carbonyl)-6-methyl-9-(tosylamino-carbonyl)-4-oxo-1,6,7,8-tetrahydro-4H-pyrido[1,2-a]pyrimidine;

3-ethoxycarbonyl-6-methyl-9-[(n-butylamino)-carbonyl]-4-oxo-1,6,7,8-tetrahydro-4H-pyrido[1,2-a]pyrimidine;

3-ethoxycarbonyl-6-methyl-9-[(4-chloro-phenyl-amino)-carbonyl]-4-oxo-1,6,7,8-tetrahydro-4H-pyrido[1,2-a]pyrimidine;

3-ethoxycarbonyl-6-methyl-9-[(3-chloro-phenyl-amino)-carbonyl]-4-oxo-1,6,7,8-tetrahydro-4H-pyrido[1,2-a]pyrimidine;

3-ethoxycarbonyl-6-methyl-9-[(3,4-dichloro-phenyl-amino)-carbonyl]-4-oxo-1,6,7,8-tetrahydro-4H-pyrido[1,2-a]pyrimidine; or 9-(phenyl-amino-carbonyl)-3-carboxy-6-methyl-4-oxo-1,6,7,8-tetrahydro-4H-pyrido[1,2-a]pyrimidine; or a pharmaceutically acceptable salt thereof.

4. The compound defined in claim 3 which is 9-(phenyl-amino-carbonyl)-3-carboxy-6-methyl-4-oxo-1,6,7,8-tetrahydro-4H-pyrido[1,2-a]-pyridimidine; or a pharmaceutically acceptable salt thereof.

* * * * *